United States Patent [19]

Wu et al.

[11] Patent Number: 4,746,606

[45] Date of Patent: May 24, 1988

[54] BILIRUBIN-SPECIFIC ENZYME AND ITS ANALYTICAL USE

[75] Inventors: Tai W. Wu; Edward R. Scalice, both of Rochester, N.Y.

[73] Assignee: Eastman Kodak Company, Rochester, N.Y.

[21] Appl. No.: 866,845

[22] Filed: May 27, 1986

[51] Int. Cl.[4] .......................... C12Q 1/26; C12Q 1/00
[52] U.S. Cl. ............................................ 435/25; 435/4; 435/174; 435/189; 435/191; 435/814; 435/816
[58] Field of Search ................ 435/25, 4, 174, 189, 435/191

[56] References Cited

U.S. PATENT DOCUMENTS 4,211,844 7/1980 Wu ........................................ 435/25

FOREIGN PATENT DOCUMENTS 140004 5/1985 European Pat. Off. .
3402504 7/1984 Fed. Rep. of Germany .
57-159487 3/1981 Japan .
84004328 11/1984 PCT Int'l Appl. .
2146997 5/1985 United Kingdom .

OTHER PUBLICATIONS

Matsui et al–Chem. Abst., vol. 103 (1985), p. 84594c.

*Primary Examiner*—Sam Rosen
*Attorney, Agent, or Firm*—J. Lanny Tucker

[57] ABSTRACT

An enzyme preparation having specific bilirubin degrading activity is described. It is isolated from plants (e.g. artichokes) of the Compositae family. It exhibits higher specificity towards bilirubin and has higher specific activity (i.e. turnover number of moles of substrate per minute per mg of protein) than similar enzymes isolated from other sources. Assay compositions, analytical elements and methods for use of such are also described.

20 Claims, 2 Drawing Sheets

4,746,606

BILIRUBIN-SPECIFIC ENZYME AND ITS ANALYTICAL USE

FIELD OF THE INVENTION

This invention relates to an enzyme preparation having specific bilirubin degrading activity. This enzyme is isolated from a plant of the Compositae family, such as artichokes. This invention also relates to the use of such enzymes in assay compositions, analytical elements and methods.

BACKGROUND OF THE INVENTION

Bilirubin is a yellow substance which is formed in the blood as a result of degradation of hemoglobin, and is the principal pigment of bile manufactured in the liver. It has been estimated that approximately 200-230 milligrams of bilirubin and its derivatives are formed each day in a healthy human adult by the degradation of hemoglobin within the liver, spleen and bone marrow.

The diagnostic significance of bilirubin is well established. For example, an excessive amount of bilirubin within the human body, referred to as jaundice, is recognized as evidence of a variety of disease conditions, particularly diseases of the liver. In addition, jaundice often occurs in new born infants whose liver is slow to begin normal function. Thus, to facilitate early diagnosis of certain disease states and/or to actively reduce bilirubin levels, a bilirubin specific enzyme would be very useful.

Enzymes shown to be specific for bilirubin have been partially purified and characterized from fungi, as described in U.S. Pat. No. 4,211,844 (issued July 8, 1980 to Wu). However, the enzymes obtained from such sources, particularly from the mushrooms described in U.S. Pat. No. 4,211,844, noted above, have relatively modest specificity towards bilirubin. When used in crude form, the enzyme preparation has relatively low specific activity, thereby necessitating larger quantities of enzymes for providing acceptable assay results.

Hence, it would be desirable to have a highly active enzyme preparation specific to degrading bilirubin and suitable for improved bilirubin assays.

SUMMARY OF THE INVENTION

An improved bilirubin-specific enzyme preparation which is isolated from a plant of the Compositae family degrades bilirubin at a pH in the range of from about 7 to about 10 and a temperature in the range of from about 20 to about 50° C., and has a $K_m$ for bilirubin of about $1.5 \times 10^{-5}$ molar and a pH optimum of about 7.4 as measured in phosphate buffer at 37° C.

This enzyme can be used to remove bilirubin from a biological fluid, e.g. whole blood or serum. The enzyme can also be used in an assay composition for the determination of an analyte other than bilirubin in a liquid where bilirubin is present as an interferent. Such a composition comprises an interactive composition for the analyte and the enzyme described above. The enzyme thereby degrades bilirubin and reduces its interference with the determination.

This invention also includes an analytical element comprising an absorbent carrier material containing the bilirubin-specific enzyme described above. In a preferred embodiment, this element includes a support and a reagent zone containing the bilirubin-specific enzyme.

Further still, this invention provides a method for the degradation of bilirubin. This method comprises contacting a liquid suspected of containing bilirubin with the bilirubin-specific enzyme described above to degrade bilirubin.

A method for the determination of bilirubin comprises the steps of:
 (a) contacting a liquid suspected of containing bilirubin with the bilirubin-specific enzyme described above at a pH and temperature effective for the enzyme to degrade bilirubin and to produce a detectable change, and
 (b) detecting the detectable change resulting from the presence of bilirubin.

A method for the determination of an analyte other than bilirubin comprises the steps of:
 (a) contacting a liquid suspected of containing an analyte other than bilirubin and in which bilirubin is an interferent for the determination, with an interactive composition for the analyte to produce a detectable change,
 (b) prior to or during step (a), contacting the liquid with the bilirubin-specific enzyme described above, thereby reducing the potential of bilirubin interference with the detectable change produced in step (a), and
 (c) detecting the detectable change resulting from the presence of the analyte.

The advantages of the present invention are provided by using a bilirubin-specific enzyme obtained from a plant of the Compositae family, and preferably from artichokes. This enzyme is unexpectedly capable of acting specifically on bilirubin. It has been found that the specificity of this enzyme for bilirubin is greater than the specificity of the known fungal enzyme described in U.S. Pat. No. 4,211,844 noted above. The enzyme preparation also has a relatively higher specific activity, i.e. an increased turnover number of moles of substrate (bilirubin) per minute per mg of protein.

DETAILED DESCRIPTION OF THE INVENTION

Figure 1:
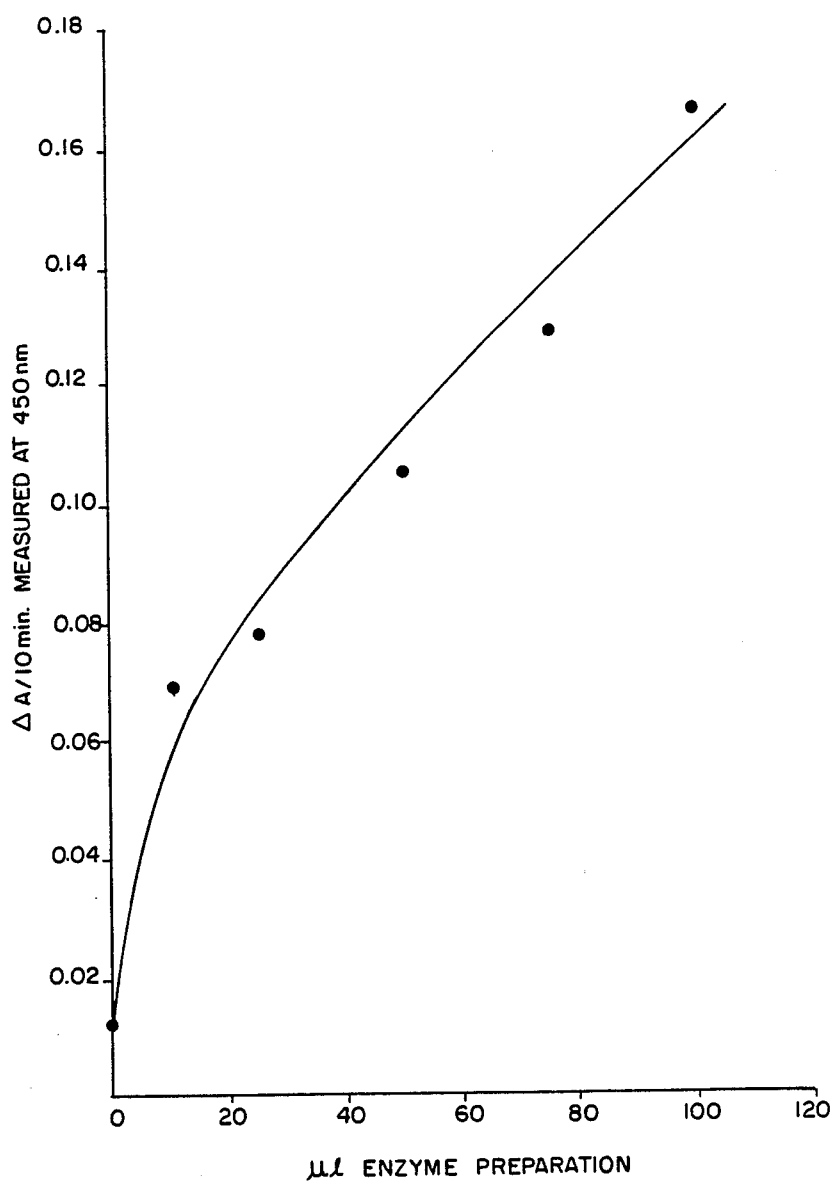
FIG. 1 is a graphical plot illustrating the change in bilirubin degradation velocity in response to the change in amount of the bilirubin-specific artichoke enzyme preparation of this invention as described in Example 2 below.

The bilirubin-specific enzymes useful in this invention can be extracted from plants of the Compositae family. Examples of such plants of the Compositae family are artichokes (*Cynara spp.*), sunflowers (*Helianthus annuus*), cardoons (*Cynara cardunculus*), lettuce (*Lactuca sativa*), chicory (*Cichorium intybus*) and dandelion (*Taraxacum officinale*). Most preferred is the enzyme extracted from artichokes. As is understood in the art, the enzyme preparation of this invention can be in a substantially pure or crude (i.e. impure) form.

The enzymes described herein can be extracted from the desired plants by any suitable extraction method. Two such methods are described in detail in U.S. Pat. No. 4,211,844 noted above, the disclosure of which is incorporated herein by reference in its entirety. A useful extraction procedure is described below in Example 1.

Bilirubin exhibits a characteristic absorption peak ($\lambda$max) at about 440 nanometers (nm) of the electromagnetic spectrum. When the enzyme degrades bilirubin in a liquid under suitable pH and temperature conditions, the absorbance (or absorption density) at λmax decreases. This density decrease is a detectable change and can be monitored against a reference liquid which lacks bilirubin. In this manner, a liquid (e.g. an aqueous liquid) can be assayed for bilirubin.

One use of the enzyme is to degrade bilirubin in a biological fluid, e.g. whole blood, when bilirubin is present in that fluid, such as in an excessive amount. This can be done by passing the fluid through a filter device (either implanted in a patient or ex vivo) containing the enzyme. A bilirubin-binding material, e.g. albumin or a mordant, such as that described in U.S. Pat. No. 4,338,095 (issued July 6, 1982 to Wu), can be used in combination with the enzyme to remove bilirubin or the products of bilirubin degradation.

Another use of the enzyme is in a method for the determination of bilirubin in an aqueous liquid, such as a biological fluid (e.g. whole blood, plasma, sera, lymph, bile, urine, spinal fluid, sputum, sweat and the like as well as stool secretions of humans or animals).

This analytical method comprises the steps of:
(a) contacting a liquid suspected of containing bilirubin with the bilirubin-specific enzyme at a pH and temperature effective for the enzyme to degrade bilirubin and to produce a detectable change corresponding to the presence and/or concentration of bilirubin, and
(b) detecting the detectable change resulting from the presence of bilirubin.

Still another use of the enzyme is to reduce bilirubin interference in assays for analytes other than bilirubin. Such assays are usually achieved with assay compositions, elements and method using interactive compositions which, when they interact with the analyte, produce a detectable change of some type (e.g. colorimetric, potentiometric, etc.). Any suitable interactive composition can be used in the practice of this invention. Examples of interactive compositions include enzyme-linked hydrogen peroxide detection systems, enzyme-linked NAD-NADH detection systems, redox reactions, hydrolysis reactions and others known in the clinical chemistry art.

The interactive composition useful in an assay of an analyte other than bilirubin can be any composition capable of physical, electrical, chemical or other interaction with the analyte of interest leading to a detectable change, for example, an absorbance shift or a change in absorption density, which can be related to the presence or amount of the analyte.

In this embodiment of the invention, a liquid suspected of containing the analyte and in which bilirubin is a potential interferent is contacted with the bilirubin-specific enzyme either before, or simultaneously with contact of the liquid with the interactive composition. The bilirubin-specific enzyme reduces the potential of bilirubin to interfere in the determination of the analyte.

Figure 2:
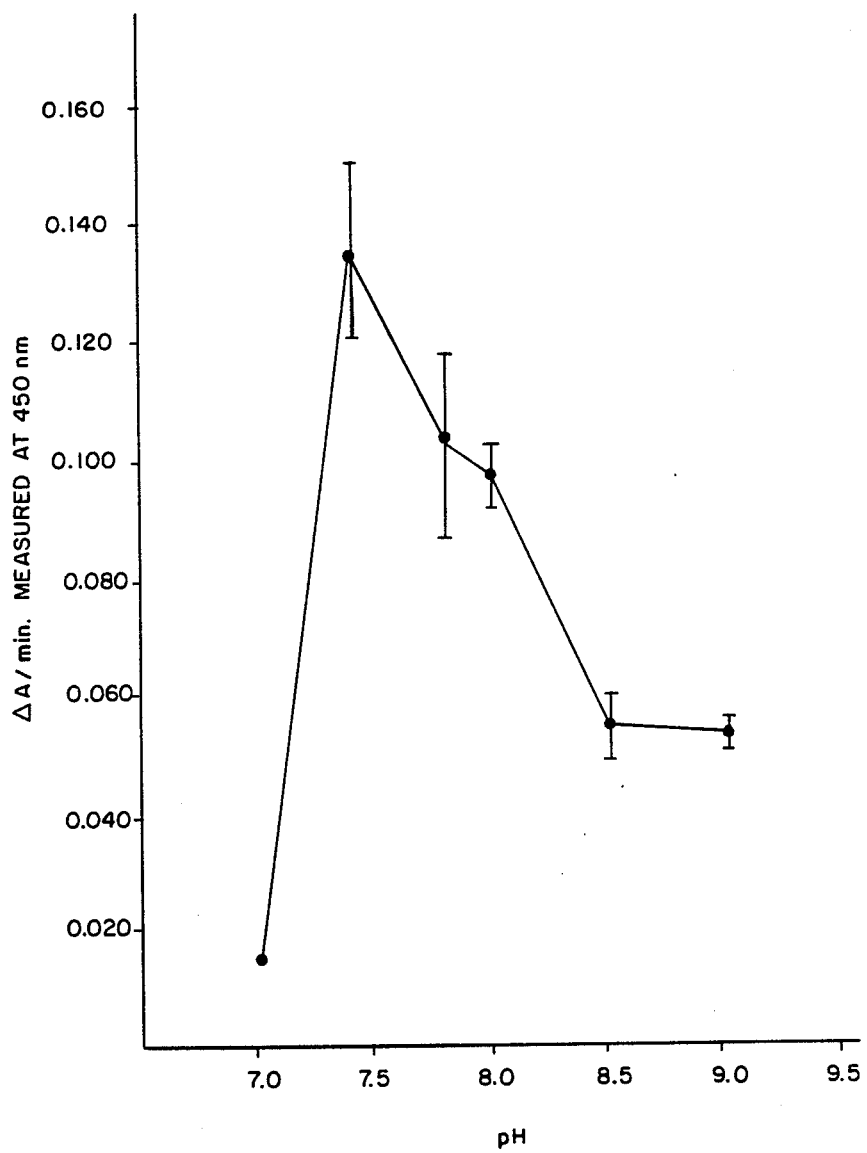
FIG. 2 is a graphical plot illustrating the effect of pH on enzyme activity as described in Example 4 below.

The enzyme useful in this invention is reactive with bilirubin within wide useful pH and temperature ranges, e.g. from about 7 to about 10 and from about 20° to about 50° C., respectively. However, it is particularly reactive in pH and temperature ranges of from about 7.5 to about 9, and from about 25° to about 45° C. The enzyme has a pH optimum of about 7.4 as determined in phosphate buffer at 37° C. (see FIG. 2).

Although it is optional, it is preferred to use a buffer with the enzyme in an assay composition. The buffer is present to maintain the pH within the useful pH range effective for bilirubin degradation. Phosphates, such as sodium phosphate, and tris(hydroxymethyl)aminomethane are particularly suitable. However, a variety of other known buffers (e.g. borates) are suitable.

The amount of the enzyme useful in the practice of this invention depends upon the bilirubin concentration of the liquid to be assayed. Generally, in solution assays, the enzyme is used in an amount in the range of from about 0.01 to about 0.2, and preferably in the range of from about 0.02 to about 0.1, milligrams per deciliter. This assumes that each mg of enzyme has the minimum activity level for bilirubin of at least 0.02 micromoles of bilirubin per minute as determined in an aqueous liquid at a pH of about 7.3 and a temperature of about 37° C. When using an enzyme of higher activity, proportionately smaller amounts of the enzyme preparations can be used.

When the bilirubin-degrading enzyme is employed to elimiante or reduce bilirubin as an interferent in an assay, the enzyme must be non-interfering with respect to the interactive composition. For example, if the analyte is to be detected using an interactive composition containing a hydrogen peroxide detection composition, it would clearly be inappropriate to use an enzyme which itself generates hydrogen peroxide. Because the enzyme preparation can be used to degrade bilirubin without generation of hydrogen peroxide, this particular problem is avoided.

The detectable change produced by the methods of this invention can be detected by a wide variety of means. For example, the methods can employ a suitable detection device capable of detecting a change in absorption density, a change in fluorescent or radioactive emission or a shift in the absorbance of a characteristic λmax.

The enzyme preparation and methods of this invention are adaptable to both solution and dry assays. In solution assays, the assay is carried out entirely in a liquid medium, and the enzyme preparation or assay composition of this invention is employed as a liquid reagent. In such cases, the enzyme preparation or assay composition is mixed with the liquid to be assayed at the desired pH and temperature. This solution assay technique is described in more detail below in Example 2.

The methods of this invention can also be practiced using a dry analytical element. The simplest element can be composed of an absorbent carrier material, e.g. a thin sheet of a self-supporting absorbent or bibulous material, such as filter paper or strips, which contains the enzyme or assay composition of this invention. The element can be divided into two or more discrete zones with different reagents incorporated into individual zones of the carrier material. Such elements are known in the art as test strips, diagnostic elements, dip sticks, diagnostic agents and the like.

Useful absorbent carrier materials are insoluble and maintain their structural integrity when exposed to water or biological fluids such as whole blood or serum. Useful elements can be prepared from paper, porous particulate structures, porous polymeric films, cellulose, glass fiber, woven and nonwoven fabrics (synthetic and nonsynthetic) and the like. Useful materials and procedures for making such elements are well known in the art as exemplified in U.S. Pat. Nos. 3,092,465 (issued June 4, 1963 to Adams et al), 3,802,842

(issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and 4,312,834 (issued Jan. 26, 1982 to Vogel et al).

Preferably, the absorbent carrier material of the dry analytical element of this invention is a porous spreading zone. This zone can be self-supporting (i.e. composed of a material rigid enough to maintain its integrity), but preferably it is carried on a separate support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (fluorescence, transmission or reflectance spectroscopy). Useful supports can be prepared from paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. Useful spreading zones can be prepared as described in U.S. Pat. Nos. 4,292,272 (issued Sept. 29, 1981 to Kitajima et al), 3,992,158 (issued Nov. 16, 1976 to Przybylowicz et al), 4,258,001 (issued Mar, 24, 1981 to Pierce et al) and 4,430,436 (issued Feb. 7, 1984 to Koyama et al) and Japanese Patent Publication 57(1982)-101760 (published June 24, 1982). It is desirable that the spreading zone be isotropically porous, meaning that the porosity is the same in each direction in the zone as caused by interconnected spaces or pores between particles, fibers, polymeric strands, etc.

The elements can have two or more discrete zones, either in the same layer or superimposed. At least one of which is preferably a porous spreading zone. The other zones can be reagent zones or registration zones as those zones are known in the art, additional spreading zones, radiation-blocking or filter zones, subbing zones, barrier zones, etc. The zones are generally in fluid contact with each other, meaning that fluids, reagents and reaction products (e.g. color dyes) can pass or be transported between superposed regions of adjacent zones. Preferably, each zone is a separately coated layer, although two or more zones can be separate areas in a single layer of the element.

The methods of this invention are then practiced by contacting (e.g. spotting) the element with a sample of the liquid to be assayed. Any detectable change which then occurs within the element is measured with appropriate apparatus. The enzyme or assay composition is present in such elements as a dried residue (e.g. a freeze-dried powder or dried residue of a coating composition).

When used in dry assays, the bilirubin-specific enzyme is generally present in an amount of from about 40 to about 400, and preferably from about 50 to about, 200 I.U./m$^2$.

The analytical elements of this invention can have at least one reagent zone containing the enzyme or assay composition of this invention. These zones can be self-supporting (i.e. composed of materials rigid enough to maintain their intergrity), but preferably they are carried on a support as described above. Any of the reagent zones of these elements can also act as a spreading zone such as those described above.

One or more zones (e.g. reagent, spreading, subbing, barrier or registration) of the elements of this invention can contain a variety of one or more other desirable, but optional components, including surfactants, enzyme activators, binders (generally hydrophilic natural or synthetic collids or polymers), hardeners, dyes, solvents, etc. These components are present in amounts known in the clinical chemistry art.

A variety of different elements, depending on the method of assay, can be prepared in accordance with the present invention. Elements can be configured in a variety of forms, including elongated tapes of any desired width, sheets or smaller chips.

The analytical method of this invention can be manual or automated. In general, the amount of bilirubin or other analyte in a liquid is determined by taking the element from a supply roll, chip packet or other source and physically contacting it with a sample of the liquid (e.g. 1 to 200 μl) so that the liquid mixes with the reagents within the element. Such contact can be accomplished in any suitable manner, e.g. dipping or immersing the element into the sample or, preferably, by spotting the element by hand or machine with a drop of the sample by pipette or another suitable dispensing means.

After sample application, the element is exposed to any conditioning, such as incubation, heating or the like, that may be desirable to quicken or otherwise facilitate obtaining any test result.

The analyte then reacts and produces a detectable change which is quantifiable with suitable apparatus. Suitable detection means include reflection or transmissive colorimetric spectrophotometry, fluorometry, radiometry, chemiluminescence, enzyme labeling, measurement of enthalpy changes and the like.

The examples below further illustrate the invention. The following information is common to the examples.

Protein concentration was determined by the method of Warburg & Christian (*Biochem. Z.*, 310:384, 1941) using a ratio of absorbances measured at 280 and 260 nm. Unless otherwise stated, all enzyme preparation extraction steps were carried out at 0°–4° C. and all chemicals were reagent grade and were obtained from Eastman Kodak Co. (Rochester, N.Y., U.S.A.). Unconjugated bilirubin used obtained from Sigma Chemical Co. (St. Louis, Mo., U.S.A.). Ditaurobilirubin was obtained from Porphyrin Products (Logan, Utah, U.S.A.). A bilirubin (unconjugated form) stock solution (100 mg/ml) was prepared by dissolving the weighted, solid material (prewet with about 100 μl of 0.1 normal NaOH) in 0.05 molar sodium phosphate buffer (pH 7.45) in a 100 ml flask. This solution was kept at 0°–4° C. under a nitrogen-enriched atmosphere. A molar absorptivity of $55 \times 10^3$ l/mole/cm at 440 nm was used for bilirubin (see method of Jacobsen & Wennberg, *Clin. Chem.*, 20:783, 1974). Just prior to use, the bilirubin stock solution was diluted with 0.05 molar of the sodium phosphate buffer.

Bilirubin-containing solutions, buffered as stated above were incubated with an aliquot of the enzyme preparation and the decrease in absorption density at λmax (440 nm) was monitored against a reference solution of identical composition but without bilirubin. The final volume of each reaction mixture was 1.01 ml. All assays were monitored at 22°–25° C. on a commercially available spectrophotometer at 440 nm, unless otherwise stated.

EXAMPLE 1

Extraction of Enzyme from Artichokes

Artichokes were rinsed with distilled water, sliced and added to 3-4 volumes of ice-chilled 0.05 molar sodium phosphate buffer (pH 7.45). The plant tissues were then homogenized with a standard blender with 10-12 separate bursts, each burst lasting 10-15 seconds, interspersed with 30-second periods of icebath chilling. The resulting homogenate was filtered through 3 layers of cheesecloth. The filtrate was then centrifuged in a standard centrifuge at 9,000 xg and 4° C. for 15-20 minutes. The resulting pellet, exhibiting negligible bilirubin-specific activity, was discarded, and the supernatant was treated with sufficient ammonium sulfate to provide 60% saturation. The resulting solid precipitate was suspended in the same buffer as above, but at pH 7.4, and 5 ml of the suspension was heated at 65° C. for 3 minutes. Recovery was carried out by dialysis overnight against water at 0°-4° C. This yielded an aqueous enzyme preparation containing about 1 to about 10 mg/ml protein and exhibiting the bilirubin-specific activity characteristic of the preparation of this invention.

EXAMPLE 2

Bilirubin Degradation in Solution Assay as a Function of Enzyme Concentration Different amounts (10-100 μl) of the enzyme preparation obtained from artichokes by the procedure described in Example 1 were added to separate 2.5 ml liquid samples containing 2 mg/dl ditaurobilirubin dissolved in 0.05 molar tris(hydroxymethyl)aminomethane buffer (pH 8.0) at 37° C. The change in absorbance at 450 nm was monitored against a reference of identical composition but without bilirubin using a standard spectrophotometer. The change in absorbance ($\Delta A$) in 10 minutes versus enzyme preparation volume is plotted in FIG. 1.

EXAMPLE 3

Bilirubin Degradation in Solution Assay as a Function of Bilirubin Concentration An aliquot containing 0.09 mg of artichoke enzyme preparation obtained as described in Example 1 was added to bilirubin-containing liquid sammples having concentrations of bilirubin ranging from $2.8 \times 10^{-6}$ to $2 \times 10^{-5}$ moles/l. Test conditions were the same as those described in Example 2. As determined from these tests, the apparent extrapolated Michaelis Constant, Km, of the artichoke bilirubin-specific enzyme preparation is about $1.5 \times 10^{-5}$ molar (i.e., about 0.9 mg/dl) (see Lineweaver & Burk, *J.A.C.S.*, 56, p. 658, 1934). This Km value implies a higher affinity for bilirubin by the artichoke enzyme relative to the fungal enzyme of U.S. Pat. No. 4,211,844 (Km of about 7.04 mg/dl or $1.2 \times 10^{-4}$ molar).

EXAMPLE 4

Enzyme Activity Dependence Upon pH

This example shows the effect of pH on the activity of the bilirubin degrading enzyme described herein.

An aqueous sample containing 2 mg/dl of unconjugated bilirubin was mixed at various pH values with 2 mg/ml of artichoke enzyme preparation of Example 1, and the enzymatic activity was measured at 37° C. The results are plotted in FIG. 2 as the net change in absorbance per minute ($\Delta A$/min), or initial velocity, over a pH range at 450 nm. From this plot, it is apparent that the optimum pH is about 7.4 in phosphate buffer at 37° C. The useful pH range is from about 7 to about 10. At the optimum pH and this stage of purity (crude preparation), the specific activity of the enzyme was about 0.024 $\Delta\mu$moles/min/mg or 0.0048 $\Delta A$/min/mg. This is about five times the specific acitivty of the fungal enzyme preparation described in U.S. Pat. No. 4,211,844, noted above, under similar conditions (see Table IV, crude extraction data, batch 2 of the patent).

The invention has been described in detail with particular reference to preferred embodiments thereof, but it will be understood that variations and modifications can be effected within the spirit and scope of the invention.

We claim:

1. A bilirubin-specific enzyme preparation isolated from a plant of the Compositae family which degrades bilirubin at a pH in the range of from about 7 to about 10 and a temperature in the range of from about 20° to about 50° C., and has a $K_m$ for bilirubin of about $1.5 \times 10^{-5}$ molar and a pH optimum of about 7.4 as measured in phosphate buffer at 37° C.

2. The preparation of claim 1 wherein said enzyme preparation is isolated from artichokes.

3. An assay composition for the determination of an analyte other than bilirubin in a liquid suspected of containing an analyte and in which bilirubin is an interferent for said determination, said composition comprising an interactive composition for said analyte and a bilirubin-specific enzyme isolated from a plant of the Compositae family which degrades bilirubin at a pH in the range of from about 7 to about 10 and a temperature in the range of from about 20° to about 50° C., has a $K_m$ for bilirubin of about $1.5 \times 10^{-5}$ molar and a pH optimum of about 7.4 as measured in phosphate buffer at 37° C., and reduces bilirubin interference with said determination.

4. The assay composition of claim 3 further comprising a buffer.

5. The assay composition of claim 3 wherein said enzyme is isolated from artichokes.

6. An analytical element comprising an absorbent carrier material containing a bilirubin-specific enzyme isolated from a plant of the Compositae family which degrades bilirubin at a pH in the range of from about 7 to about 10 and a temperature in the range of from about 20° to about 50° C., has a $K_m$ for bilirubin of about $1.5 \times 10^{-5}$ molar and a pH optimum of about 7.4 as measured in phosphate buffer at 37° C.

7. The element of claim 6 further comprising a support carrying said absorbent carrier material.

8. The element of claim 6 wherein said enzyme is isolated from artichokes.

9. The element of claim 6 further comprising an interactive composition for an analyte other than bilirubin.

10. A dry analytical element for the determination of an analyte other than bilirubin comprising a nonporous susport having thereon a reagent zone containing an interactive composition for an analyte other than bilirubin and a bilirubin-specific enzyme isolated from a plant of the Compositae family which degrades bilirubin at a pH in the range of from about 7 to about 10 and a temperature in the range of from about 20° to about 50° C., has a $K_m$ for bilirubin of about $1.5 \times 10^{-5}$ molar and a pH optimum of about 7.4 as measured in phosphate buffer at 37° C.

11. The dry element of claim 10 wherein said enzyme is isolated from artichokes.

12. A method for the degradation of bilirubin comprising contacting a liquid suspected of containing bilirubin with a bilirubin-specific enzyme to degrade bilirubin, said enzyme isolated from a plant of the Compositae family and which degrades bilirubin at a pH in the range of from about 7 to about 10 and a temperature in the range of from about 20° to about 50° C., has a $K_m$ for bilirubin of about $1.5 \times 10^{-5}$ molar and a pH optimum of about 7.4 as measured in phosphate buffer at 37° C.

13. The method of claim 12 wherein said liquid is whole blood.

14. A method for the determination of bilirubin comprising the steps of:
    (a) contacting a liquid suspected of containing bilirubin with a bilirubin-specific enzyme at a pH and temperature effective for said enzyme to degrade bilirubin and to produce a detectable change, said enzyme isolated from a plant of the Compositae family and which degrades bilirubin at a pH in the range of from about 7 to about 10 and a temperature in the range of from about 20° to about 50° C., has a $K_m$ for bilirubin of about $1.5 \times 10^{-5}$ molar and a pH optimum of about 7.4 as measured in phosphate buffer at 37° C., and
    (b) detecting the detectable change resulting from the presence of bilirubin.

15. The method of claim 14 carried out with an analytical element containing said enzyme.

16. The method of claim 14 wherein said enzyme is isolated from artichokes.

17. A method for the determination of an analyte other than bilirubin comprising the steps of:
    (a) contacting a liquid suspected of containing an analyte other than bilirubin and in which bilirubin is an interferent for said determination with an interactive composition for said analyte to produce a detectable change,
    (b) prior to or during step (a), contacting said liquid with a bilirubin-specific enzyme isolated from a plant of the Compositae family which degrades bilirubin at a pH in the range of from about 7 to about 10 and a temperature in the range of from about 20° to about 50° C., has a $K_m$ for bilirubin of about $1.5 \times 10^{-5}$ molar and a pH optimum of about 7.4 as measured in phosphate buffer at 37° C., thereby reducing the potential of bilirubin interference with said detectable change produced in step (a), and
    (c) detecting the detectable change resulting from the presence of said analyte.

18. A method for the extraction of a bilirubin-specific enzyme comprising:
    (a) blending at least part of a plant of the Compositae family with an aqueous buffer solution having a pH of from about 6.8 to about 7.8 to form a homogeneous aqueous mixture,
    (b) separating insoluble solids from said aqueous mixture to obtain an aqueous liquid supernatant,
    (c) treating said supernatant to produce a precipitate,
    (d) suspending said precipitate in an aqueous buffer solution having a pH of from about 6,8 to about 7.8 to form a suspension,
    (e) heating said suspension above about 22° C. but below the boiling point thereof, and
    (f) cooling said suspension and separating solids from said suspension to recover an aqueous liquid supernatant containing an enzyme which is bilirubin-specific,
    each of said steps (a), (b), (c), (d) and (f) carried out at a temperature of from about $-10°$ C. to about 4° C.

19. A method for the extraction of a bilirubin-specific enzyme comprising:
    (a) blending at least part of a plant of the Compositae family with an aqueous buffer solution having a pH of from about 6.8 to bout 7.8 to form a homogeneous aqueous mixture,
    (b) separating insoluble solids from said aqueous mixture to obtain an aqueous liquid supernatant,
    (c) treating said supernatant to produce a precipitate,
    (d) suspending said precipitate in an aqueous buffer solution having a pH of from about 6.8 to about 7.8 to form a suspension,
    (e) treating said suspension with a water-miscible organic liquid chilled to a temperature effective to produce a precipitate from said resulting aqueous-organic liquid mixture,
    (f) repeating said steps (d) and (e) at least one time using as said precipitate in said repeat of step (d) the precipitate produced in step (e), and
    (g) recovering the precipitate remaining following the last repeat of step (e) to obtain an enzyme which is bilirubin-specific.

20. The method of claim 19 wherein said plant is artichoke.

* * * * *